United States Patent
Smith

(10) Patent No.: US 9,642,883 B2
(45) Date of Patent: May 9, 2017

(54) ***LACTOBACILLUS RHAMNOSUS* AND *BIFIDOBACTERIUM ANIMALIS* SUBSP. *LACTIS* FOR USE IN PREVENTION OR TREATMENT OF UPPER RESPIRATORY TRACT INFECTIONS**

(71) Applicant: Chr. Hansen A/S, Hoersholm (DK)

(72) Inventor: Tracey Jane Smith, Medway, MA (US)

(73) Assignee: Chr. Hansen A/S, Hoersholm (DK)

( * ) Notice: Subject to any disclaimer, the term of this patent is extended or adjusted under 35 U.S.C. 154(b) by 156 days.

(21) Appl. No.: 14/371,888

(22) PCT Filed: Jan. 14, 2013

(86) PCT No.: PCT/EP2013/050552
§ 371 (c)(1),
(2) Date: Jul. 11, 2014

(87) PCT Pub. No.: WO2013/104783
PCT Pub. Date: Jul. 18, 2013

(65) Prior Publication Data
US 2015/0118190 A1   Apr. 30, 2015

(30) Foreign Application Priority Data
Jan. 13, 2012 (EP) .................... 12151148

(51) Int. Cl.
*A61K 35/74* (2015.01)
*A61K 35/745* (2015.01)
*A61K 35/747* (2015.01)
*A61K 35/742* (2015.01)

(52) U.S. Cl.
CPC .......... *A61K 35/745* (2013.01); *A61K 35/742* (2013.01); *A61K 35/747* (2013.01)

(58) Field of Classification Search
None
See application file for complete search history.

(56) References Cited

U.S. PATENT DOCUMENTS

| | | | |
|---|---|---|---|
| 7,862,808 B2 * | 1/2011 | Isolauri | A23L 1/3014 424/93.3 |
| 2008/0107634 A1 * | 5/2008 | Mogna | A61K 35/741 424/93.45 |

FOREIGN PATENT DOCUMENTS

| WO | WO-2006/007526 | 1/2006 |
|---|---|---|
| WO | WO-2006/054135 | 5/2006 |

OTHER PUBLICATIONS

Stephenson, Terrence "How children's responses to drugs differ from adults" Brit. J. Clin. Pharmacol. 2005, 59(6), 670-673.*
Barrett, B. "Wisconsin Upper Respiratory Symptom Survey (WURSS)" retrieved online<www.fammed.wisc.edu/wurss/>, 2004 (archived Aug. 29, 2006, accessed Nov. 28, 2016), 3 pages.*
Barrett, B. "Wisconsin Upper Respiratory Symptom Survey (WURSS)" retrieved online<www.fammed.wisc.edu/wurss/>, 2015, (accessed Nov. 28, 2016), 11 pages.*
NIH "Fecal Recovery of the Probiotic Bacteria *Lactobacillus rhamnosus* GG (LGG) and *Bifidobacterium animalis* Subspecies *lactis* BB-12 (BB-12) in Healthy Humans Following Daily Consumption of a Probiotic Supplement (LGG BB-12)", NIH/NLM-ClinicalTrials.gov ID: NCT01757054, Oct. 29, 2013, 9 pages.*
Bresson, J-L, et al "Scientific Opinion of the Panel on Dietetic Products, Nutrition and Allergies on a request from Valio Ltd on the scientific substantiation of a health claim related to LGG® MAX and reduction of gastro-intestinal discomfort." The European Food Safety Authority (EFSA) Journal, Oct. 30, 2008, 853, pp. 1-15.*
Latvala, S, et al "Potentially probiotic bacteria induce efficient maturation but differential cytokine production in human monocyte-derived dendritic cells" World J Gastroenterol, Sep. 28, 2008, 14(36), pp. 5570-5583. doi:10.3748/wjg.14.5570.*
Kajander, K, et al "Clinical trial: multispecies probiotic supplementation alleviates the symptoms of irritable bowel syndrome and stabilizes intestinal microbiota" Aliment Pharmacol Ther, 2008, 27, 48-57. doi:10.1111/j.1365-2036.2007.03542.x.*
Barrett et al. "Validation of a short form Wisconsin Upper Respiratory Symptom Survey (WURSS-21)", Health Quality of Life Outcomes, 7, pp. 76-96, Aug. 12, 2009.
Berggren et al. "Randomised, double-blind and placebo-controlled study using new probiotic lactobacilli for strengthening the body immune defence against viral infections", European Journal of Nutrition, 50, pp. 203-210, Aug. 28, 2010.
Collado et al. "Probiotic strains and their combination inhibit in vitro adhesion of pathogens to pig intestinal mucosa", Current Microbiology, vol. 55, pp. 260-265, Jul. 2007.
de Vrese et al., "Probiotic bacteria stimulate virus-specific neutralizing antibodies following a booster polio vaccination", European Journal of Nutrition, 44, pp. 406-413, Dec. 1, 2004.
International Search Report issued in connection with International Application No. PCT/EP2013/050552 dated Jun. 13, 2013.
Ouwehand et al., "The mucus binding of *Bifidobacterium lactis* Bb12 is enhanced in the presence of lactobacillus GG and *Lact. delbrueckii* subsp. *bulgaricus*", Letters in Applied Microbiology, vol. 30, pp. 10-13, Jan. 2000.

(Continued)

Primary Examiner — Chris R Tate
Assistant Examiner — Aaron J Kosar
(74) Attorney, Agent, or Firm — Foley & Lardner LLP

(57) ABSTRACT

The present invention relates to a composition comprising *Lactobacillus rhamnosus*, preferably strain ATCC53103, and *Bifidobacterium animalis* subsp. *lactis*, preferably strain DSM 15954, for use in reducing the duration and/or severity of upper respiratory tract infection (URI) in teenagers and adults. Further aspects of the invention relate to a composition comprising *Lactobacillus rhamnosus* and *Bifidobacterium animalis* subsp. *lactis* for use in increasing the Health-Related Quality of Life (HRQL) in teenagers and adults having upper respiratory tract infection (URI), for reducing at least one and preferably several such as two, three, four or all of the symptoms of sore throat, scratchy throat, cough, hoarseness, chest congestion and for reducing the median severity score in teenagers and adults having upper respiratory tract infection (URI).

11 Claims, 10 Drawing Sheets

(56) References Cited

OTHER PUBLICATIONS

Rafter et al., "Dietary synbiotics reduce cancer risk factors in polypectomized and colon cancer patients", The American Journal of Clinical Nutrition, vol. 85, pp. 488-496, Feb. 2007.

Rautava et al., "Specific probiotics in reducing the risk of acute infections in infancy—a randomised, double-blind, placebo-controlled study", British Journal of Nutrition, 101, pp. 1722-1726, Nov. 6, 2008.

Wickens et al., "A differential effect of 2 probiotics in the prevention of eczema and atopy: A double-blind, randomized, placebo-controlled trial", Journal of Allergy and Clinical Immunology, vol. 122, pp. 788-794, Sep. 2008.

\* cited by examiner

Figure 1:
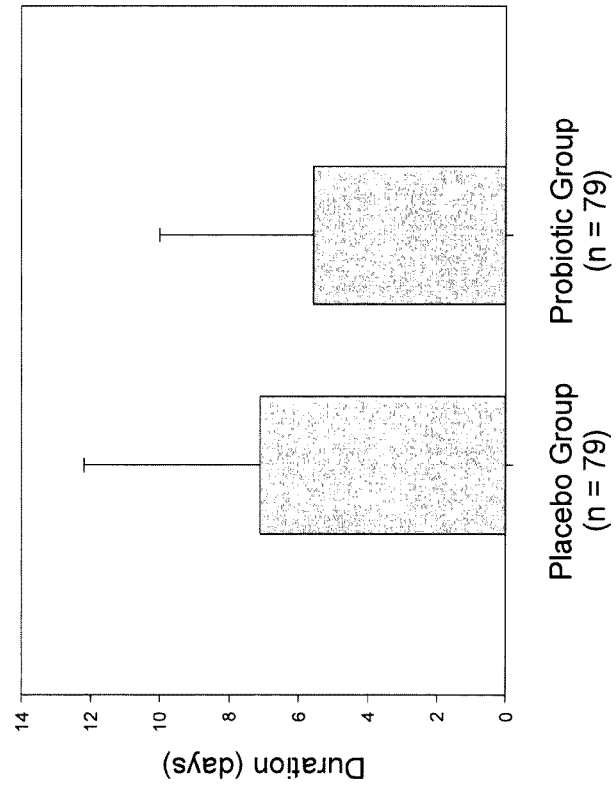

Figure 1. Mean Duration of URIs in the placebo and probiotics groups

Duration of URIs in the total sample and by group

| Total Sample (N = 158) | | | | Placebo (n = 79) | | | | Probiotic (n = 79) | | | |
|---|---|---|---|---|---|---|---|---|---|---|---|
| Mean | Median | SD | Range | Mean | Median | SD | Range | Mean | Median | SD | Range |
| 6.35 | 5.00 | 4.80 | 2-25 | 7.11 | 6.00 | 5.07 | 2-25 | 5.58 | 4.00 | 4.41 | 2-21 |

Figure 2:
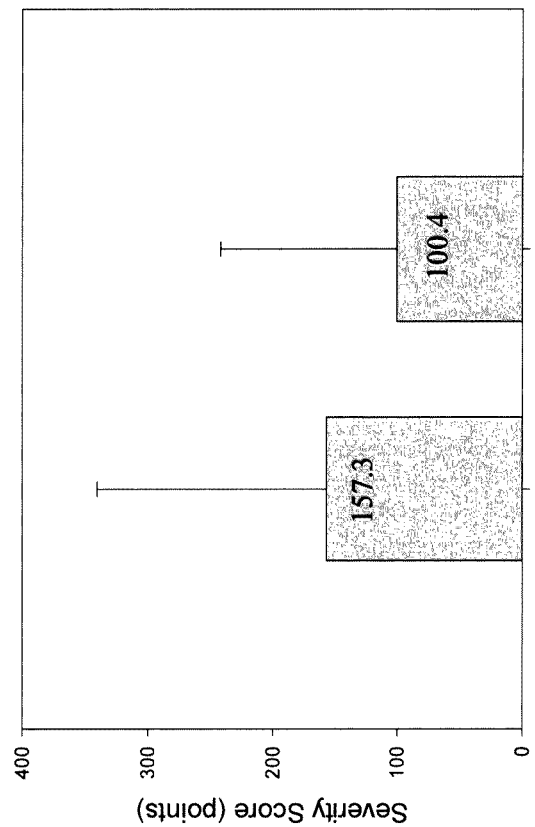

Figure 2. Mean Severity of URIs in the placebo and probiotics groups

Severity scores* of URIs in the total sample and by group

| Total Sample (N = 143) | | | | Placebo (n = 69) | | | | Probiotic (n = 74) | | | |
|---|---|---|---|---|---|---|---|---|---|---|---|
| Mean | Median | SD | Range | Mean | Median | SD | Range | Mean | Median | SD | Range |
| 127.87 | 66.00 | 164.69 | 5-832 | 157.30 | 88.00 | 183.39 | 6-801 | 100.43 | 58.00 | 140.88 | 5-832 |

Figure 3:
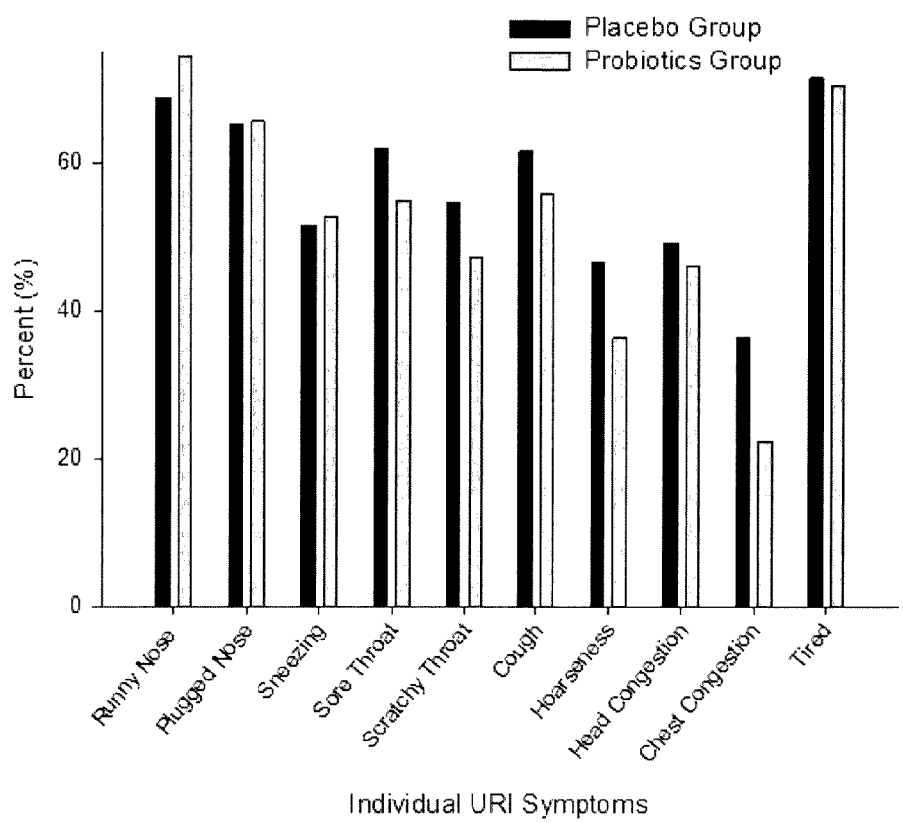

*Severity scores were generated by the WURSS-21 and encompassed symptoms and their impact on daily life Figure 3. Frequency of individual URI symptoms. Height of bars reflects the percentage of surveys that indicated presence of URI symptoms.

LACTOBACILLUS RHAMNOSUS AND BIFIDOBACTERIUM ANIMALIS SUBSP. LACTIS FOR USE IN PREVENTION OR TREATMENT OF UPPER RESPIRATORY TRACT INFECTIONS

FIELD OF THE INVENTION

The present invention relates to a composition comprising *Lactobacillus rhamnosus*, such as the strain deposited as ATCC 53103, and *Bifidobacterium animalis* subsp. *lactis*, such as the strain deposited as DSM 15954, for use in reducing the duration and severity of upper respiratory tract infection (URI), such as the common cold, in teenagers and adults and for increasing the Health-Related Quality of Life (HRQL) in teenagers and adults having upper respiratory tract infection (URI).

BACKGROUND OF THE INVENTION

Respiratory tract infections (RTIs), defined as any infection of the respiratory tract, are a leading cause of non-institutionalized illness and result in burden on the healthcare system and associated costs. Upper respiratory infections (URIs) are RTIs that affect the upper airway. URIs are the most common type of RTI and are predominantly viral with less than 15% attributable to bacteria. The estimated incidence of viral URIs in adults residing in the United States (U.S.) is approximately 2.5 episodes per person annually, which burdens the healthcare system and negatively impacts productivity at work and school.

The term "common cold" is often used interchangeably with URIs by the general public; however, the medical community defines the common cold as a clinical illness wherein expression of symptoms results from a viral-induced URI (Barrett et al., 2009). In terms of a medical diagnosis, the ICD9 code terminology classifies acute nasopharyngitis/common cold as code 460. Psychological stress and poor mental health (e.g., depression, anxiety, and exhaustion) has been associated with higher risk for acquiring URIs. Typical symptoms of URIs include sneezing, nasal discharge or obstruction, sore or scratchy throat, hoarseness, and cough; headache, myalgia, malaise and fever may also be present. Symptom severity typically peaks 2-3 days after infection, with a mean duration of approximately one week with 25% of cases lasting longer. URIs can exacerbate pre-existing conditions such as asthma, or can lead to other illnesses such as otitis media, sinusitis, or a lower RTI (i.e. bronchitis, bronchiolitis, tracheitis and pneumonia).

Despite the viral etiology of most URIs, antibiotics are commonly prescribed to treat symptoms, a practice that contributes to antibiotic drug resistant bacterial strains. There is no evidence that over-the-counter (OTC) drugs have any effect on the duration of the viral infection, and they offer only marginal benefits with regard to alleviation of symptoms. Further, OTC drugs may have unwanted side effects, such as drowsiness, xerostomia (dry mouth), nervousness, irritability, difficulty sleeping, and elevated blood-pressure. More serious consequences with OTC drugs are also possible. For example: liver toxicity due to co-ingestion of acetaminophen and alcohol, and gastrointestinal bleeding or renal toxicity in response to aspirin and non-steroidal anti-inflammatory agents.

Characteristics of URI symptoms (for example, duration and severity), and functional impairment in response to symptoms, impact health-related quality of life (HRQL) during URIs (Barrett et al., 2009). Various aspects of HRQL can be negatively affected during URIs, such as: physical functioning, bodily pain, vitality, social functioning and mental health. Thus, there is interest in strategies that can improve HRQL in persons suffering from URIs.

The administration of probiotics, defined by the World Health Organization as "live organisms which when administered in adequate amounts confer a benefit on the host" is a safe nutrition intervention in the generally healthy population. Probiotics are found in the human intestinal tract and commonly present in yogurt and other food items (e.g., beverages, cereals and chocolate candy bars).

Probiotics have been investigated for their ability to modulate immune function, and positively impact clinical outcomes related to atopic allergies, respiratory allergies, RTIs, gastrointestinal diseases, periodontal infections, and female urogenital conditions. Oral supplementation of certain probiotic strains has demonstrated immunomodulatory effects in healthy adults.

Probiotic strains may help prevent and treat RTIs in children and adults. However, there are some limitations to the prior art findings. For example: sample sizes were too small to detect differences between groups with regard to incidence rates; some studies did not differentiate URIs from lower RTIs; results were confounded by the use of prebiotics; and severity has only been assessed in two studies of normal healthy adults (Bergren et al., 2011; and de Vrese et al., 2005).

The only published study on a composition of *Lactobacillus rhamnosus* GG and *Bifidobacterium animalis* subsp. *lactis* for use in the treatment of respiratory infections relate to infants (Rautava et al., 2009, and WO2006007526). The study by Rautava et al., 2009, was a randomized, double-blind, placebo-controlled trial in 81 infants using an infant formula containing *Bifidobacterium lactis* Bb-12 and *Lactobacillus rhamnosus* GG for up to 12 months and a formula without probiotics as a control. Incidence of recurrent (≥3) RTIs was lower in response to probiotics versus placebo (P=0.031). Rautava et al., 2009, found that the incidence of acute otitis media as a consequence of URIs was lower in response to probiotics versus placebo (P=0.027). The duration or severity was not registered.

The study did not report on severity of RTIs. Further, the study is not generalizable to an adult population due to inherent differences between the immune systems of children, in particular infants, and adults.

A number of published studies have investigated the efficacy of probiotics in reducing the incidence, duration and severity of URIs in adults. These studies provide evidence that certain probiotic strains may be effective in reducing the duration and severity of URIs and RTIs in generally healthy adults, when compared to non-probiotic controls. None of these studies were made with a composition comprising the combination of *Lactobacillus rhamnosus* GG and *Bifidobacterium animalis* subsp. *lactis*.

Mixed results in the published probiotic studies underscore the notion that not all probiotics are created equal, and the beneficial effects of probiotics on URI outcomes appear to be strain specific and may work optimally in combination.

SUMMARY OF THE INVENTION

The primary purpose of the study was to assess the effect of the composition comprising the specific probiotics *Lactobacillus rhamnosus* GG and *Bifidobacterium animalis* subsp. *lactis* (BB-12®) on HRQL in teenagers and adults having upper respiratory tract infection and whether this combination would be beneficial for improving the HRQL in persons suffering from URIs. Assessing multiple factors of HRQL during URIs—including the symptom status (severity and duration) and functional status—is warranted since URIs negatively impact productivity.

Multiple measures of HRQL were investigated during URIs, such as: self-reported duration, symptoms and functional status. Secondary outcomes explored the self-reported incidence of URIs, and missed school and work days due to URIs. It was found that a composition comprising *Lactobacillus rhamnosus* GG and *Bifidobacterium animalis* subsp. *lactis* (BB-12®) could be used in reducing the duration and severity of upper respiratory tract infection (URI) in teenagers and adults and that the composition comprising LGG® and BB-12® also beneficially affects HRQL during URIs and minimize missed school days due to URIs.

The study's findings that frequency and incidence of URIs did not differ between groups are similar compared to previously published studies in adults (de Vrese et al., 2005) whereas Berggren et al. (2011) found that the frequency of URIs (≥1 URI) was significantly lower in the probiotics group compared to the placebo group (91 vs. 76 URIs, respectively). Conflicting results between Berggren et al. (2011) and the current study may be attributed to different probiotic strains (*L. casei* DN-114 and *L. plantarum/L. paracasei* versus LGG® and BB-12®, respectively).

One prior study detected no significant differences in total severity scores between groups (Berggren et al., 2011), while de Vrese et al. (2005) reported that total severity scores were lower in response to probiotics compared to placebo (P=0.056, P=0.057, and P<0.01, respectively). The reduction in severity scores in the present study was more pronounced compared to the aforementioned trial (52% versus 20-40%, respectively) (de Vrese et al., 2005). Probiotic strains were different between studies, which may explain dissimilar results.

LEGEND OF THE FIGURES

FIG. 1. Mean Duration of URIs in the placebo and probiotics groups

FIG. 2. Mean Severity of URIs in the placebo and probiotics groups

FIG. 3. Frequency of individual URI symptoms. Height of bars reflects the percentage of surveys that indicated presence of URI symptoms.

Figure 4:
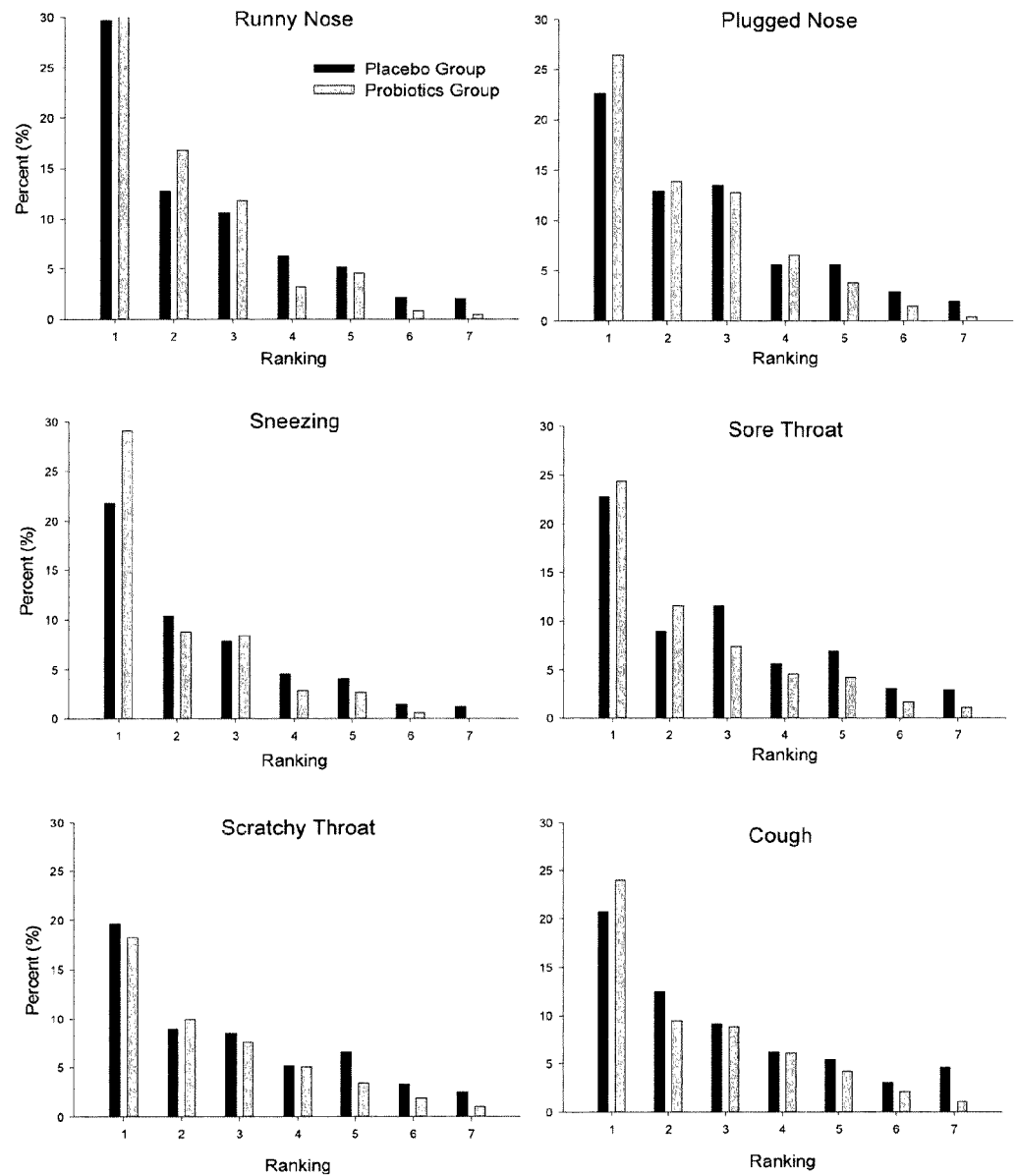
Figure 4:
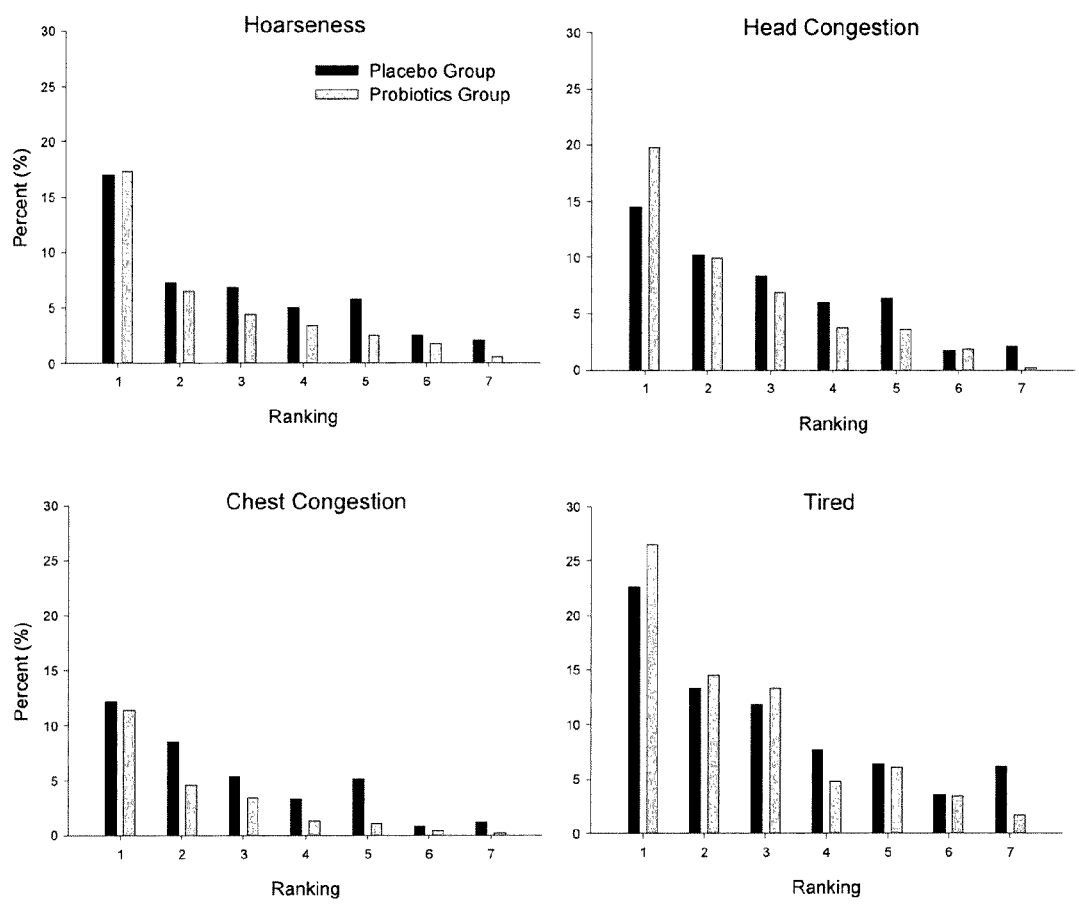

FIG. 4. Frequency of individual URI symptoms, ranked on a 7-point Likert-Type scale (1=very mild, 7=severe). Height of bars reflects the percentage of surveys at each ranking. Graphs do not show the percentage of subjects who did not report the symptom. Percentages are representative of the total number of surveys available for the placebo group (n=475) and probiotics group (n=518). For "runny nose", 29.7% and 36.6% of surveys in the placebo and probiotics group, respectively, indicated a ranking of "1".

Figure 5:
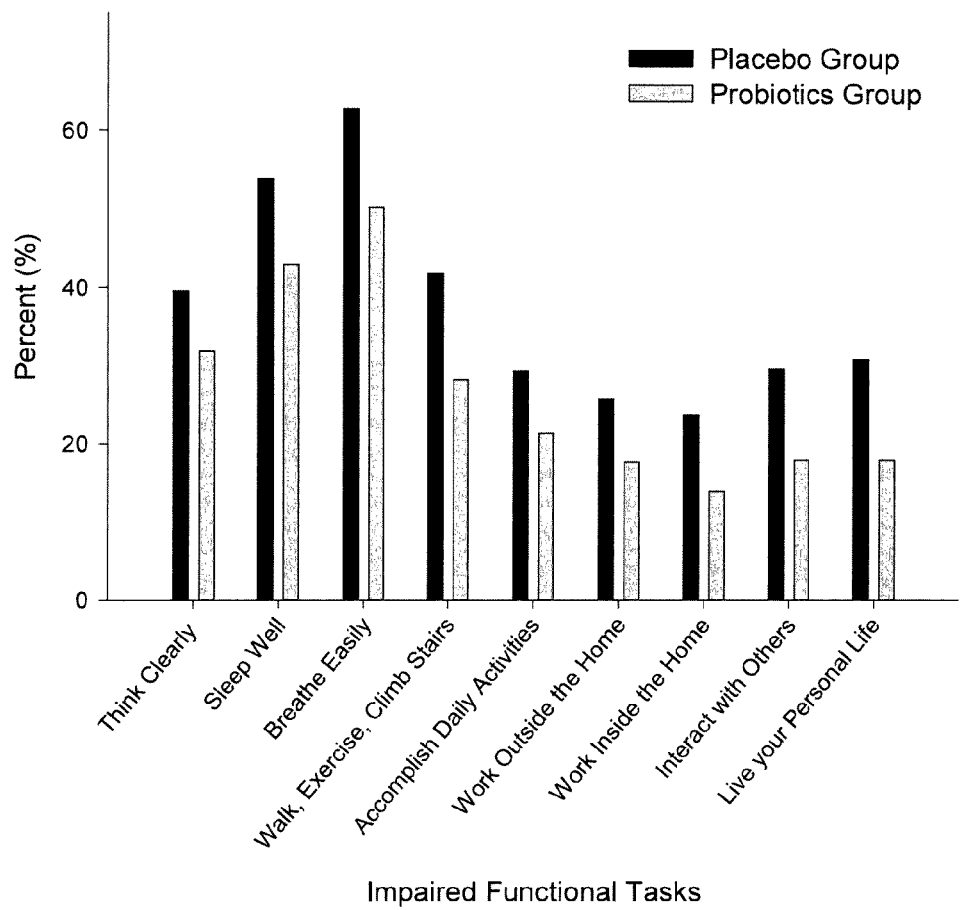

FIG. 5. Frequency of impaired functional tasks due to URIs. Height of bars reflects the percentage of surveys that indicated an impaired functional task.

Figure 6:
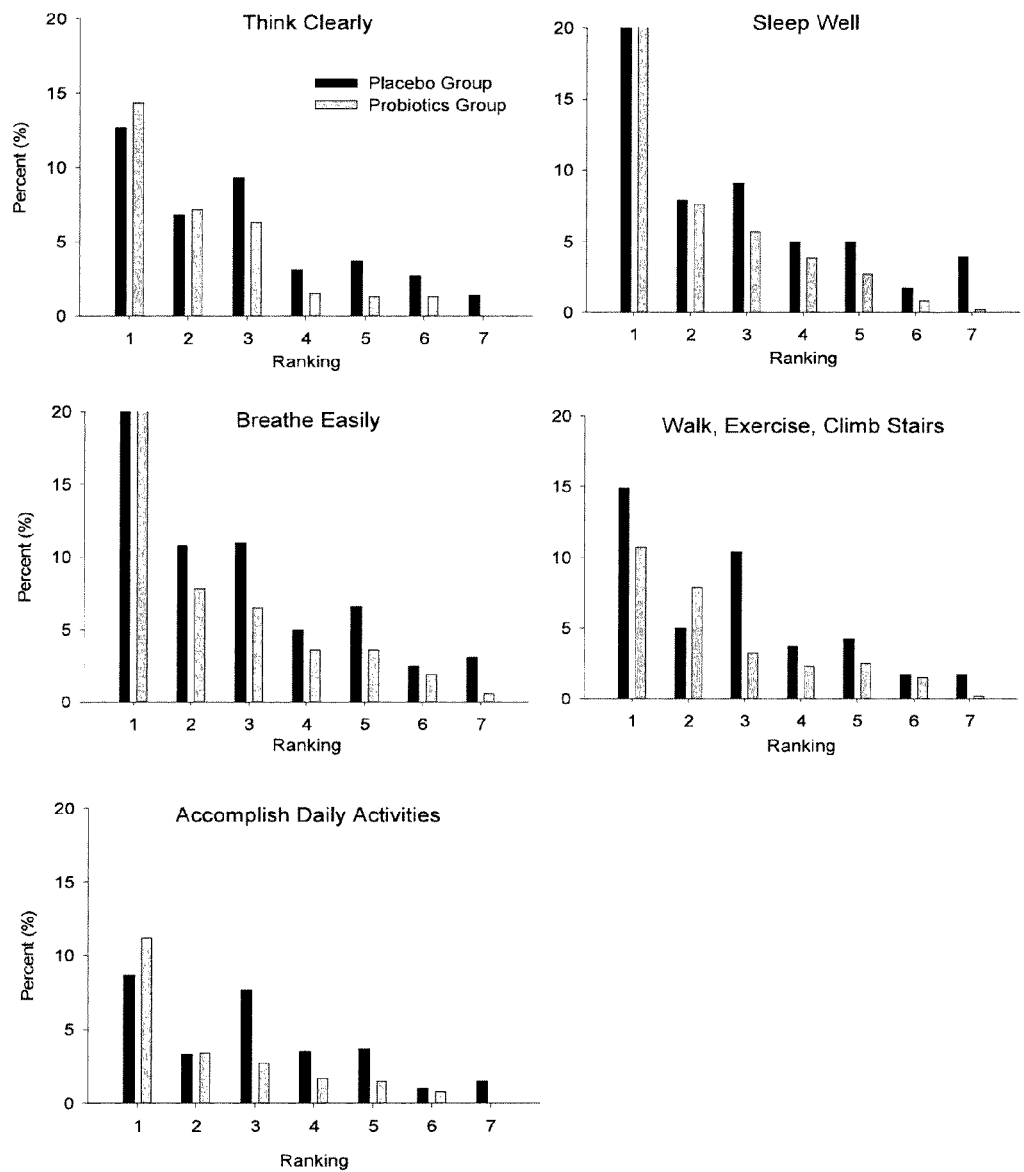
Figure 6:
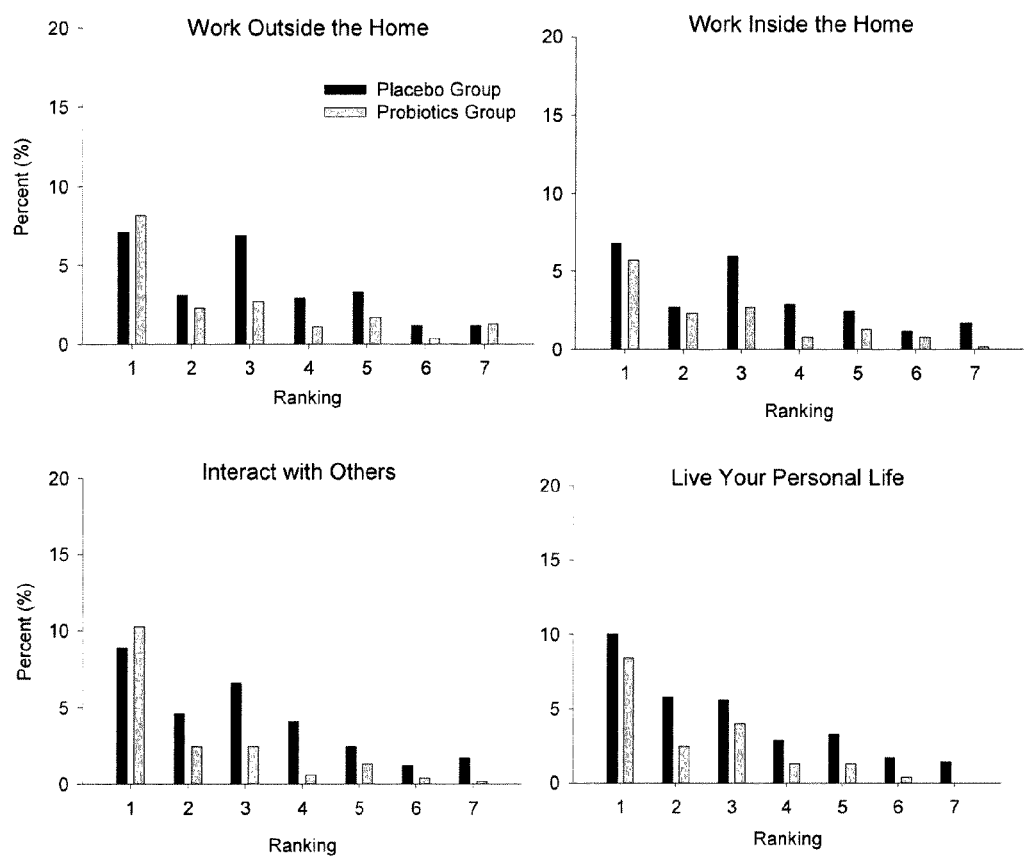

FIG. 6. Frequency of impaired functional tasks due to URIs, ranked on a 7-point Likert-Type scale (1=very mildly; 7=severely). Height of bars reflects the percentage of surveys at each ranking. Graphs do not show the percentage of subjects who did not report the functional task. Percentages are representative of the total number of surveys available for the placebo group (n=475) and probiotics group (n=518). For "sleep well", 21.2% and 22.1% of surveys in the placebo and probiotics group, respectively, indicated a ranking of "1". For "breathe easily", 23.7% and 26.0% of surveys in the placebo and probiotics group, respectively, indicated a ranking of "1".

Figure 7:
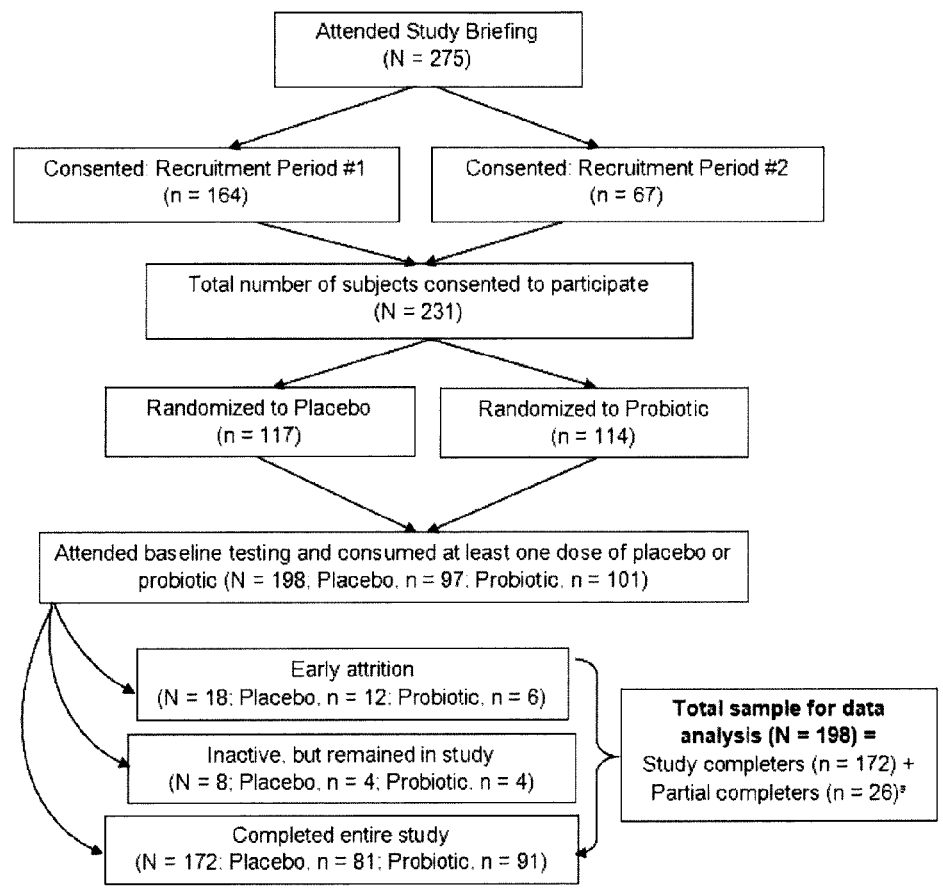

FIG. 7. Recruitment and retention of subjects.

<sup>a</sup>The 26 partial completers include the 18 subjects who attrited from the study prior to week 12, and the eight subjects who remained in the study, but who were inactive for a portion of data collection.

Figure 8:
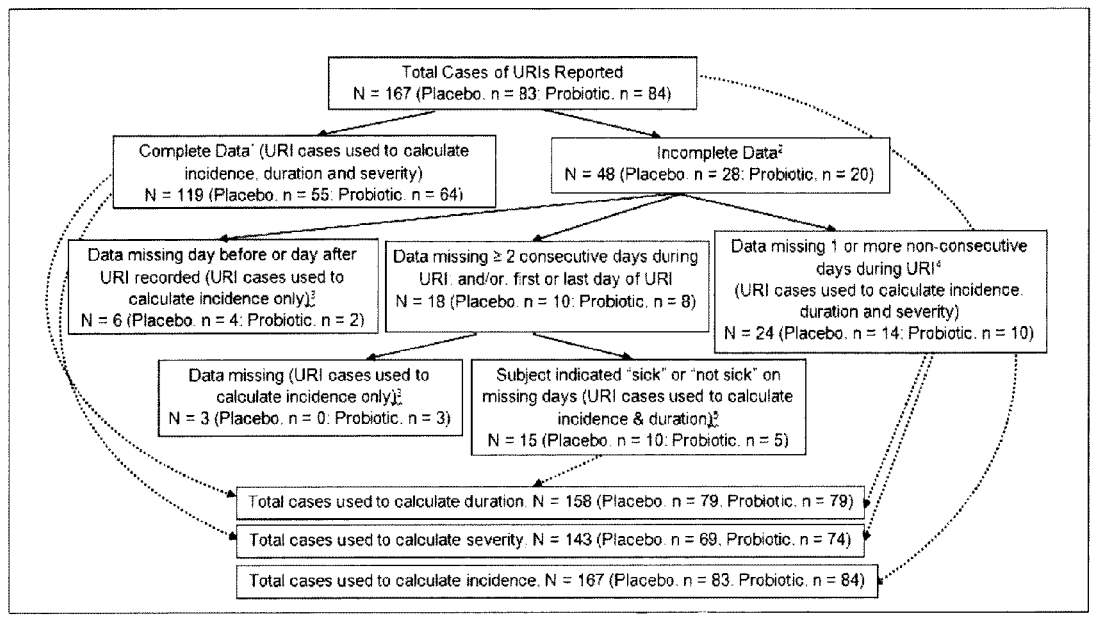

FIG. 8. Available data from Daily WURSS-21.

Note: solid lines indicate the flow from each box to the subordinate box(es); dotted lines indicate the data that contributed to the total cases used to calculate duration, severity and incidence of URIs.

[1]Complete data=no missing data during URI; no missing data the day before or day after a URI was recorded;

[2]Incomplete data=data missing during URI, or data missing the day before or day after a URI was recorded;

[3]Survey data used to calculate incidence only, and excluded for duration and severity analyses

[4]Missing severity score(s) interpolated using data from the day before and day after the missing survey

[5]Survey data excluded for severity analyses

DEFINITIONS

For the purpose of the present specification and claims, the following terms are defined as follows:

"Adults" refers to generally healthy humans of the age of 18 and above.

"Common cold" is defined as a clinical illness wherein expression of symptoms results from a viral-induced URI (Barrett et al., 2009). For the purposes of this patent application, self-reported incidence of the "common cold" was captured via an affirmative response to question #1 of the WURSS-21 two days in a row. Thus, in the present context this term is used synonymously with the term "URI" defined below.

"HRQL during URI episodes" was measured in two ways, as: 1) self-reported duration of URI episodes ascertained by the WURSS-21; and, 2) self-reported symptom severity score combined with the functional status score ascertained via the WURSS-21. HRQL with regard to duration was expressed in terms of days and HRQL with regard to symptom severity and functional status was expressed in terms of area-under-the-curve, which was ascertained by adding daily WURSS-21 scores across all days of the illness (Barrett et al., 2009).

"Infant" generally refers to a human from about birth to 12 months of age.

"Infant formula" refers to a composition in liquid or powdered form that satisfies the nutrient requirements of an infant by being a substitute for human milk. These formulations are regulated by EU and US regulations which define macronutrient, vitamin, mineral and other ingredient levels in an effort to simulate the nutritional and other properties of human breast milk.

"Missed school days" is defined as the total number of days that a subject missed any classes in a given day due to a URI.

"Missed work days" is defined as the total number of days that a subject missed any paid work, internship or practicum due to a URI.

"Preventing" means stopping or hindering a disease, disorder, or symptom of a disease or condition through some action.

"Self-reported duration of URI episodes" was defined as the number of days a subject experiences a URI episode as indicated by the WURSS-21. Start of illness was indicated by affirmative response to question #1 on the WURSS-21 two days in a row, while the end of illness was indicated by a negative response to question #1 of the WURSS-21 two days in a row (Barrett et al., 2009). Duration of the URI episode was calculated from the first day of an affirmative response to the first day of a negative response.

"Self-reported functional status" was defined as the degree that a URI interfered with the subject's ability to complete activities of daily living (such as sleeping and exercising) and social role activities (such as interacting with others), ranging from "very mildly" to "severely" as indicated by the WURSS-21.

"Self-reported incidence of URI episodes" was defined as the number of URI episodes experienced by each subject during the data collection period expressed in categories (zero, at least one, at least two, at least three, etc. . . . ) and as a continuous variable (mean number or URI episodes per subject).

"Self-reported severity of URI symptoms" was defined as the degree of discomfort of a URI symptom ranging from "very mild" to "severe" as indicated by the WURSS-21.

"Therapeutically effective amount" refers to an amount that results in an improvement or remediation of the disease, disorder, or symptoms of the disease or condition.

"Treating" means ameliorating, improving or remedying a disease, disorder, or symptom of a disease or condition.

"Upper Respiratory Infection (URI)" was defined as reporting affirmatively to question #1 of the WURSS-21 ("How sick do you feel today?") for 2 days in a row. Thus, in the present context this term is used synonymously with the term "common cold".

"Wisconsin Upper Respiratory Symptom Survey (WURSS-21)" is a 21-item survey designed to measure changes in HRQL indices over time, specifically patient-valued illness domains related to the common cold, that may be modifiable in response to an intervention (Barrett et al., 2009). The developers of the WURSSs make a distinction between URIs as a "disease" category used by health professionals, and the common cold as an "illness" term used by the general public. This semantic difference is the cornerstone of the surveys, which were designed to assess symptom status and functional status indicators that are important to patients during common cold episodes. The full 44-item version (WURSS-44) and the shorter 21-item version (WURSS-21) are designed to be administered daily and assess HRQL during common cold episodes by taking into account symptom status and functional status. The WURSS-44 contains the 21-items that are in the WURSS-21, but has 21 additional symptom and functional status items. In the course of determining the construct validity of the WURSS-44, a 21-item version of the survey emerged, termed the WURSS-21. The symptom and functional status items of the WURSS-44 with the highest "importance" ratings were included in the WURSS-21 (Barrett et al., 2009). The WURSSs appear to be the most appropriate tools for assessing outcomes of interest in the study of the present patent application. Since the WURSS-21 performs similarly compared to the WURSS-44, and takes less time to complete, this shorter version was chosen for assessing outcomes in the study of the present patent application.

"Teenagers" refers to generally healthy humans of the age of 13 to 19 years.

DETAILED DESCRIPTION OF THE INVENTION

To determine the effect of the composition comprising the specific probiotics *Lactobacillus rhamnosus* GG and *Bifidobacterium animalis* subsp. *lactis* (BB-12®) on HRQL, the WURSS-21 was used to assess duration and severity of URIs, considering both symptom severity and functional status impairment. It was found that the median duration of URIs in the probiotics group was significantly shorter by 2 days compared to the placebo group. Thus, in a first aspect, the invention relates to a composition comprising *Lactobacillus rhamnosus* and *Bifidobacterium animalis* subsp. *lactis* for use in reducing the duration of upper respiratory tract infection (URI) in teenagers and adults.

The frequency and incidence of URIs in this study was not different between the placebo and probiotics groups. These findings are contrary to some prior studies in children that have documented a reduced incidence in URI symptoms or RTI episodes. The current study varied from this prior trial with regard to the study sample (infants versus adults), which precludes a comparison of findings.

In order to determine HRQL during URIs, this study assessed both symptom severity and the impact of symptoms on daily life using the WURSS-21. The median severity score for the placebo group in this study was 88 points, while the median severity scores was 58 points in the probiotics group. It was found that the probiotics group had significantly fewer days of illness and significantly lower severity scores which indicate a higher HRQL in the probiotics group as compared to the placebo group. Also, the probiotics group missed significantly fewer school days compared to the placebo group.

Thus, a second aspect of the invention relates to a composition comprising *Lactobacillus rhamnosus* and *Bifidobacterium animalis* subsp. *lactis* for use in reducing the severity of upper respiratory tract infection (URI) in teenagers and adults and a third aspect of the present invention relates to a composition comprising *Lactobacillus rhamnosus* and *Bifidobacterium animalis* subsp. *lactis* for use in increasing the Health-Related Quality of Life (HRQL) in teenagers and adults having upper respiratory tract infection (URI).

It is not possible to compare these results to others studies employing probiotics, since prior trials did not use the WURSS-21.

The current study found that median duration of URIs was approximately two days (50%) lower in the probiotics group compared to the placebo group (p=0.001). The mean duration of URIs for the placebo group was six days; therefore, this finding has practical implications since a two day reduction represents 33% of the total URI duration.

The current study also found that median severity of URIs was significantly lower in the probiotics group compared to the placebo group by approximately 52% (p=0.0003). These findings have practical implications since severity scores took into account both symptom severity and the negative impact of URI symptoms on functional tasks. The reduction in severity scores in the current study was pronounced compared to studies using other strains (de Vrese et al., 2005). These results underscore the notion that the beneficial effects of probiotics appear to be strain specific.

It is feasible that the students attended school regardless of URIs, since the incidence of missed school days was low relative to the URI infection rate (84%); however, it is also possible that subjects may not have had classes scheduled on days that they were sick. The current study found that the probiotics group missed significantly fewer school days compared to the placebo group (mean difference=0.2 days).

In this study, approximately 6% of subjects (n=12) reportedly missed work, and a total of 19 days of work were missed, due to a URI. It is premature to draw conclusions about the number of missed work days due to URIs, since subjects were not asked about their employment status during the data collection period. It is possible that students were motivated to earn money and attended work regardless of a URI.

A higher percentage of subjects in the placebo group reported interference with functional tasks compared to the probiotics group; and, most individual symptoms were reported by a higher percentage of subjects in the placebo group compared to the probiotics group. Also, a higher percentage of subjects in the probiotics group versus the placebo group ranked symptoms as less severe (score of one, two, three or four points on the 7-point Likert-type scale); and, a higher percentage of subjects in the placebo group versus the probiotics group ranked symptoms and functional tasks as more severe (score of five, six or seven on the 7-point Likert-type scale). No other studies used the WURSS-21 to assess differences in symptom severity and functional status impairment in response to probiotics versus placebo, thus no comparisons were made. These observations are likely responsible for the significantly higher WURSS-21 scores in the placebo group versus the probiotics group (p=0.0003). These findings have practical implications. For example, URIs appear to have less impact on activities of daily life in subjects who took probiotics compared to placebo.

Further aspects of the invention relate to a composition comprising *Lactobacillus rhamnosus* and *Bifidobacterium animalis* subsp. *lactis* for use in reducing at least one and preferably several such as two, three, four or all of the symptoms of sore throat, scratchy throat, cough, hoarseness, chest congestion in teenagers and adults having upper respiratory tract infection (URI).

The present invention also relates to a composition comprising *Lactobacillus rhamnosus* and *Bifidobacterium animalis* subsp. *lactis* for use in reducing the median severity score in teenagers and adults having upper respiratory tract infection (URI).

Findings are not generalizable to other probiotic strains. However, it is contemplated that it is generalizable to mutants and variant of the strains used in the combination. Examples of strains of *Bifidobacterium animalis* subspecies *lactis* are strains selected from the group consisting of CHCC5445 (BB-12®) with accession number DSM 15954 and mutant and variants thereof, such as CHCC7158 (HN019, deposit number DSM17280). This strain was isolated from a commercially available infant formula product labeled Fernleaf DR-10 bifidus that was sold in Taiwan during 2000.

In the present context, the term "mutant" should be understood as a strain derived from one of the strains used in the combination by means of e.g. radiation and/or chemical treatment. The mutant should be a functionally equivalent mutant of *Bifidobacterium animalis* subspecies *lactis* deposited as DSM15954 or of *Lactobaccillus rhamnosus* deposited as ATCC 53103. Especially, the term "mutant" refers to a strain obtained by subjecting a strain (such is a strain of the combination) to any conventionally used mutagenization treatment including treatment with a chemical mutagen such as ethane methane sulphonate (EMS) or N-methyl-N'-nitro-N-nitroguanidine (NTG), UV light or to a spontaneously occurring mutant. A mutant may have been subjected to several mutagenization treatments (a single treatment should be understood one mutagenisation step followed by a screening/selection step), but it is presently preferred that no more than 20, or no more than 10, or no more than 5, treatments are carried out. In a presently preferred mutant, less that 5%, or less than 1% or even less than 0.1% of the nucleotides in the bacterial genome have been shifted with another nucleotide, or deleted, compared to the mother strain. The mutant or variant should belong to the same species as the mother strain.

Additionally, since the current study assessed the combination of *Lactobacillus rhamnosus* GG and *Bifidobacterium animalis* subsp. *lactis* (BB-12®) findings are not generalizable to the probiotic strains independent of one another.

The findings reported in the present patent application are based upon a subgroup of generally healthy adults having the ages of 18 to 25 years but are considered applicable to generally healthy teenagers and adults including elderly, i.e. adults of the age of above 70 years. The study was performed on not pregnant women, but it is contemplated that the results will also be applicable to pregnant women. The composition may be particularly useful for persons at risk of acquiring a URI such as persons under psychological stress or having poor mental health as outline above.

In the present invention, the form of administration of *Lactobacillus rhamnosus* and *Bifidobacterium animalis* subsp. *lactis* is not critical as long as a therapeutically effective amount is administered to the person in need thereof.

Compositions prepared in accordance with the invention may be administered in the form of foods or of dietary supplements. They may, for example, be dairy products, and in particular fermented dairy products comprising at least said strains, optionally combined with other lactic acid bacteria, for example with yogurt ferments, or other food products such as a snack bar, or beverages such as juice.

The *Bifidobacterium animalis* subsp. *lactis* and *Lactobacillus rhamnosus* can also be provided as a dietary supplement in the form of a powder, tablet, such as a lozenge or effervescent tablet, in capsular form, as a component of an emulsion or a paste, or in any other suitable carrier determined by those of skill in the art to be an effective carrier for live microorganisms. Compositions comprising *Bifidobacterium animalis* subsp. *lactis* and *Lactobacillus rhamnosus* can be in individual sachets, capsules, chewing gum, or in more general compositions such as oil drops.

The composition for use according to the invention preferably comprises *Lactobacillus rhamnosus* GG deposited as strain ATCC 53103, and *Bifidobacterium animalis* subsp. *lactis* (BB-12®) deposited as DSM 15954. *Lactobacillus rhamnosus* GG and *Bifidobacterium animalis* subsp *lactis* BB-12® are commercially available from Chr. Hansen A/S, Hoersholm, Denmark and from American Type Culture Collection (ATCC) and Deutsche Sammlung von Mikroorganismen and Zellkulturen GmbH (DSMZ), respectively.

Compositions prepared in accordance with the present invention can be used in the context of the prevention and treatment of upper respiratory infection (URI), and in particular of the common cold. Preferably, in order to obtain an optimal effect, they should be administered daily for at least one week, and advantageously for a longer period such as at least 2 weeks, at least 4 weeks, at least 6 weeks, at least 9 weeks, and preferably 12 weeks as in the present study, in an amount corresponding to at least $10^6$, such as at least $10^7$, preferably at least $10^8$, generally between $10^9$ and $10^{12}$ of both *Lactobacillus rhamnosus* and *Bifidobacterium animalis* subsp. *lactis*.

In another aspect, the present invention relates to a method for reducing the duration and/or severity of upper respiratory tract infection (URI) in teenagers and adults, the method comprising administering to the teenager or adult a therapeutically effect amount of *Lactobacillus rhamnosus* and *Bifidobacterium animalis* subsp. *lactis*. Evidently, all the aspects and embodiments described above also relate to this aspect.

EXAMPLES

The study was a prospective, randomized, double-blind, placebo-controlled trial. The primary purpose of this study was to assess the effect of LGG® and BB-12 on HRQL during URIs. The population sample was a random sample of college students living on campus in residence halls at FSU (Framingham, Mass.) between Jan. 17, 2011 and May 11, 2011. The investigators adhered to FSU's Policy Regarding Use of Human Subjects in Research (Log #ACC07-08/030 A004) (Framingham State University Insitutional Review Board, 2010) and UMDNJ's Policy on Protection of Human Subjects (00-01-05-10:10) (University of Medicine and Dentistry of New Jersey Institutional Review Board, 2006a).

All students living on campus in residence halls at FSU (Framingham, Mass.) in January 2011 were invited to participate in the study. Subjects were excluded from participation and asked not to sign the consent form, if: 1) their driver's license or state identification card indicated that they were under 18 years of age or over 25 years of age; 2) they experienced chronic perennial allergies (such as, allergies to dust or mold); 3) they were pregnant; or 4) they had been diagnosed with asthma, Type 1 diabetes, chronic fatigue syndrome, human immunodeficiency virus (HIV) or acquired immunodeficiency syndrome (AIDS) (since these medical conditions affect immune function). Medically-related exclusion criteria were also stated in the Screening Form, which students were asked to complete after signing the consent form and before baseline data collection occurred.

Subjects were excluded from participation and asked not to sign the consent form, if: 1) their driver's license or state identification card indicated that they were under 18 years of age or over 25 years of age; 2) they experienced chronic perennial allergies (such as, allergies to dust or mold); 3) they were pregnant; or 4) they had been diagnosed with asthma, Type 1 diabetes, chronic fatigue syndrome, human immunodeficiency virus (HIV) or acquired immunodeficiency syndrome (AIDS) (since these medical conditions affect immune function). Medically-related exclusion criteria were also stated in the Screening Form, which students were asked to complete after signing the consent form and before baseline data collection occurred. Students were also excluded from participation and asked not to sign the consent form if they had acute pancreatitis; if they were undergoing treatment for cancer; or, were taking immunosuppressive drugs for an autoimmune disease or post-transplant. Subjects were asked to refrain from consuming non-study-related dietary supplements containing probiotics (e.g., Culturelle®) and specialty yogurts (for example, DanActive™ or Activia™) during the study as well as Airborne® and any herbal preparations containing the following ingredients: Echinacea, quercitin, Goldenseal, Propolis, and umchaloabo. This information was listed on the consent form and stated during the initial study briefing. Subjects were reminded of dietary restrictions on a weekly basis after completing the weekly questionnaire.

Two study recruitment periods were held in order to maximize participation, which are herein referred to as Recruitment Period #1 and Recruitment Period #2. Daily for 12 weeks, subjects were asked to consume probiotics or placebo sticks and complete the WURSS-21. Once per week, subjects were also asked to complete the Weekly Questionnaire. Subjects completed all of the aforementioned surveys via the online application, "Survey Monkey" (www.surveymonkey.com). Subjects met with the study staff once every two to three weeks (to accommodate the academic calendar) during the Spring, 2011 semester to obtain a two or three week supply of probiotics/placebo. Daily, subjects were asked to send a text message to the designated mobile number stating that they had taken their probiotic/placebo and completed the survey(s). If a subject had limited text messaging capabilities, or were having problems with their mobile phone, they were allowed to report daily compliance via email. Study staff recorded compliance with the probiotic/placebo and questionnaire(s) on the Data Collection Record when they received a text message or email. Compliance was also recorded by subjects via the following question on the daily, online survey: "Have you consumed your probiotic/placebo today?"

Subjects were reminded daily (7 days per week including weekends, holidays and Spring Break) that they must take their probiotic/placebo and complete the questionnaire(s) before 7 PM each day. Study staff followed-up with all subjects who had not sent a text message or email by 7 PM by sending them a text message or email containing the following statement, "Please consume your probiotic and take the survey [survey link], if you haven't already done so. Please reply to this message to confirm completion". Compliance and follow-up correspondence with subjects was recorded on the Data Collection Record. If the subject did not respond by midnight, then he or she was considered non-compliant for that day.

Probiotic and placebo were administered as a strawberry-flavored, powder. The powder was packaged in a small foil "stick". Each probiotic stick contained approximately 1 billion colony forming units (CFU) each of *Lactobacillus rhamnosus* subsp. LGG® and *Bifidobacterium animalis* subsp. *lactis* (BB-12®) in powder form. Placebo sticks were similar in taste and appearance to the probiotic stick, but did not contain any probiotics. Chr. Hansen A/S manufactured the probiotic and placebo sticks and labeled each stick with a number code to identify placebo or active. The subjects, principal investigator (PI), or research assistants did not know which code represented the probiotic and which code represented the placebo. The code was provided to an independent agency (Combat Feeding Directorate, Natick Soldier Research, Development, and Engineering Center, Natick, Mass.) who maintained possession of the code for the duration of the data collection period. When the data cleaning and descriptive analysis was complete, the blinding code was given to the PI. Prior storage studies have indicated that these particular probiotic strains are shelf-stable at room temperature (approximately 70 degrees Fahrenheit) for at least 12 months; however, counts of live LGG® and BB-12® were repeated within two weeks of the end of this study to ensure quality control.

Subjects were randomized to receive probiotic or control/placebo daily for 12 weeks. The PI used "GraphPad", an internet-based random number generator (GraphPad Random Number Generator, 2005), to generate the randomization list. According to the program's website, this program "is seeded with the time of day, so it works differently each time you use it. Each subject was first assigned to a group non-randomly. Then the assignment of each subject was swapped with the assignment of a randomly chosen subject" (GraphPad Random Number Generator, 2005). The entire process was repeated twice to ensure randomization. The PI generated one randomization list for the first recruitment period and another randomization list for the second recruitment period, after subjects consented to participate and before data collection began. This ensured that an equal number of subjects were randomized to the probiotic and placebo groups. Each subject's two and three week supplies were packaged in plastic zipper bags and individually-labeled with unique study identification numbers ranging from 001 up to 231 using the randomization list. These numbers corresponded to the subject numbers on each subject's data collection forms. An identified person who was not part of the study staff (i.e., student health services coordinator at FSU) maintained the randomization list indicating probiotic or placebo assignment in case a subject had to be un-blinded (e.g., in the case of a serious adverse event).

Random assignment of subjects was performed sequentially in the order in which the subjects were enrolled in the study. The PI assigned each subject a sequential number starting with and ending with 231, in the order that the consent forms were signed and returned to the PI, which was documented on a "master identification list". This number served as the unique subject identification number. All probiotics and placebo were stored in a cool, dry location (less than 70 degrees Fahrenheit) during the data collection period.

Subjects were advised to store their probiotics/placebo sticks in a cool, dry location (less than 70 degrees Fahrenheit). Subjects were advised to consume only one stick per day. If subjects forgot to take their probiotic/placebo on a given day, they were told via the consent form and Instructions for Consuming Probiotic/Placebo not to take a make-up dose the next day. Subjects were also informed via the consent form and instructions that consumption of more than one stick per day could result in gas, boating and nausea. On weekdays when subjects picked-up their new probiotics/placebo supply, they were asked to return empty and un-opened probiotic/placebo sticks from the previous two or three weeks. If subjects forgot to bring their empty or un-opened sticks, they were asked to return to their dorm room immediately to retrieve them. If this was not possible, the subject arranged an alternate meeting time with study staff to turn-in their empty or un-opened sticks. Subjects returned their last supply of empty or un-opened probiotic/placebo sticks, and picked up their final gift card, on either Thursday 28 April (Recruitment Period #1) or Wednesday 11 May (Recruitment Period #2).

The WURSS-21 was used to determine if a study participant was suffering from a URI; and, subsequently, their HRQL during the course of the URI. The WURSS-21 was administered via an online application (www.SurveyMonkey.com). The WURSS-21 is composed of one global severity item (listed first), one global change item (listed last), 10 symptom-based items (listed second through eleventh) and nine functional status items (listed twelfth through twentieth) (Barrett et al., 2009). All subjects answered question #1 of the WURSS-21, "How sick do you feel today?" each day during the data collection period. The subject was prompted to answer the remaining 20 questions if, and only if, they did not answer "not sick" to question #1.

A URI episode was recorded if the subject answered affirmatively to question #1 two days in a row. If a subject reported a URI episode within seven days of recovering from a previous URI episode (indicated by answering "no" to question #1 two days in a row) then this episode was considered as part of the previous infection. However, if a subject reported a URI episode more than seven days after recovering from a prior episode, then this episode was recorded as a new infection (Barrett et al., 2009).

Two HRQL scores were generated from the WURSS-21. The first HRQL score was related to duration of the URI episode. Self-reported duration of a URI episode was determined using responses to question #1 on the WURSS-21. Start of illness was indicated by an affirmative response to question #1 two days in a row, while the end of illness was indicated by a negative response to question #1 two days in a row (Barrett et al., 2009). Duration was calculated from the first day of an affirmative response up to (but not including) the first day of a negative response.

The second HRQL score, generated from the WURSS-21, assessed both symptom severity and functional status; and, was expressed in terms of area-under-the-curve (AUC) which was ascertained by adding daily WURSS-21 scores (the possible response range was 0-133) across all days of the illness (Barrett et al., 2009).

Subjects self-reported via the Weekly Questionnaire if they: missed any school or work (including an internship or practicum) as a consequence of a URI; or, took antibiotics or corticosteroids for any reason. Subjects were asked if they missed any classes in the previous seven days due to a URI. If they answered "yes" they were prompted to indicate how many days they missed any classes. Subjects were also asked if they missed any work in the previous seven days (including paid work, an internship or a practicum) as a consequence of a URI; and, if "yes", they were prompted to indicate how many days they missed work.

All subjects remained in the study regardless of compliance with the study intervention and completion of questionnaires. Subjects were withdrawn from study participation if the PI determined that it was not in their best interest to continue participation, e.g., if the subject reported that they were newly diagnosed with a medical condition specified in the exclusion criteria.

All study data were analyzed using IBM SPSS statistical software version 19.0 (IBM Corporation, Somers, N.Y.). Study data were entered periodically throughout the data collection period. Significance was established at $p \leq 0.05$. Outcomes in subproblems two through four were analyzed using an intent-to-treat analysis, based on guidance from the Consolidated Standards of Reporting Trials (CONSORT) Statement (Schulz et al., 2010). The intent-to-treat analysis (last observation carried forward) included all outcomes data, regardless of compliance with probiotic/placebo and attrition. For example, if a subject withdrew from the study at week eight, all cases of URI that occurred prior to attrition were included in the analyses. The analysis was carried out using data obtained during the full 12 week intervention period and, again, using data obtained during weeks 2-12 of the intervention period, since URI episodes during the first week may not adequately reflect the intervention. Subjects' data were excluded if they consumed any antibiotics or steroids at any time during the data collection period. For the analysis with regard to compliance with the intervention, subjects' data were included during the weeks in which they consumed their probiotic/placebo at least 5 times. If a subject failed to complete the two or more days in a row, and did not communicate whether or not they were suffering from a URI on those days, the data were considered "missing".

Health-Related Quality of Life: Duration of URI

If a subject failed to complete the during a URI episode, but indicated they were suffering from a URI the day before and day after the missed day, then it was assumed they were suffering from a URI on the missed day; and, the missed day was then included in the duration calculation. This assumption was made based on three factors: 1) clinical observations indicating that symptoms typically persist daily until resolution; 2) 'end of illness' was defined by a subject answering 'not sick' to question #1 two days in a row (Barrett et al., 2009); and, 3) the assumption was equally applied to both groups, thus limiting bias.

Health-Related Quality of Life: Severity of URI

If a subject missed the two or more days in a row during a URI episode, or failed to complete the survey on the first or last day of a URI episode, then a symptom severity/functional status score was not calculated for that URI. In other cases where a subject missed the on one or more non-consecutive days during a URI episode, the missing day's severity score was interpolated by averaging the severity score from the day before and day after the missing data point. This assumption was made since the severity of URI symptoms appears to change over time in a linear fashion (Barrett et al., 2009); and, the assumption was equally applied to both groups thus limiting bias.

Two HRQL scores were generated from the WURSS-21. The first HRQL score was related to duration of the URI episode and the second HRQL score assessed both symptom severity and functional status. The first and second HRQL scores were reported in the total sample and within each continuous variable expressed as number of days and the mean AUC for each URI episode, respectively. The AUC is calculated by adding daily scores (responses may range from 0-133) across all days of the illness (Barrett et al., 2009). Each URI was considered a separate case, for example, if subject #50 had two URIs during the data collection period, then each URI was reported separately. Descriptive statistics (mean, median, range, and standard deviation) were reported for these continuous variables. Normal distribution of continuous variables was assessed using the Shapiro-Wilk statistic. A p-value less than or equal to 0.05 indicates a departure from normal. If data were normally distributed, the differences between the probiotics and placebo groups was determined using Independent samples T-test. If data were not normally distributed, data were analyzed using the Mann-Whitney U test, the non-parametric equivalent of an Independent T-test.

Results

Two-hundred and thirty-one subjects consented to participate in the study, and were randomized to Placebo or Probiotic. Of the 231 subjects who initially enrolled in the study, 14% (n=33; Placebo, n=20, 61% Probiotic, n=13, 39%) failed to attend the baseline testing session and/or consume at least one dose of placebo or probiotic. The aforementioned subjects were not included in any data analyses. Of the 231 subjects who initially enrolled, 86% (n=198; Placebo, n=97, 49%; Probiotic, n=101, 51%) attended baseline testing and consumed at least one dose of placebo or probiotic; and, this describes the intent-to-treat sample, referred to as the total sample for the remainder of this document. Of these 198 subjects, the retention rate was 91% (N=180; Placebo, n=85, 47% Probiotic, n=95, 53%).

Of the 198 subjects in the total sample, 4% (n=8; Placebo, n=4, 50%; Probiotic, n=4, 50%) were inactive for some portion of the data collection period (i.e., they failed to pick up new supplies of probiotics/placebo and/or did not take the daily surveys). These eight subjects chose not to withdraw from the study; and, their data from the weeks of active participation were included in the statistical analysis.

A total of 43 adverse events (AEs) were reported during the study period. None of the adverse events met the criteria for an unanticipated problem per 45 CFR part 46 as specified in UMDNJ IRB's Form titled, "Unanticipated Problems/Adverse Events in Human Subjects Research Report to IRB" (University of Medicine and Dentistry of New Jersey Institutional Review Board, 2006b).

Of the 43 AEs reported, self-diagnosed viral gastrointestinal infection was the most commonly reported (n=19, 44%; Placebo, n=9, 47%; Probiotic, n=10, 53%), which can be expected given that the study was conducted during the winter months when the incidence of acute viral gastroenteritis is highest. Increased flatulence and bloating are known potential side effects associated with the consumption of probiotics, and were the second most common adverse event occurring in 16% of subjects (n=7; Placebo, n=4, 57%; Probiotic, n=3, 43%).

The results from Mann-Whitney U tests for BMI, age, weight, and waist circumference demonstrated that these characteristics did not differ significantly between groups (p>0.05). Results from the Independent samples t-test indicated that height did not significantly differ between groups. (t=1.344(196), p=0.181).

Seventy-six percent (n=151) of the subjects in the total sample were female; and, Fisher's exact test indicated that the distribution of males and females did not significantly differ between the probiotic and placebo groups (p=0.242).

Fisher's exact test indicated that the distribution of races did not significantly differ between the probiotic and placebo groups (p=0.185). The majority of subjects (83%, n=165) in the total sample (N=198), classified themselves as 'White or Caucasian'. Pearson chi-square test indicated that the distribution of ethnicities (i.e., 'White or Caucasian', 'Black or African American', and 'Other') did not significantly differ between the groups ($X^2$=0.283(2), p=0.868).

Of the 198 subjects in the total sample, 39% (n=77; Placebo, n=39, 51%; Probiotic, n=38, 49%) did not experience any URIs. In the remaining 61% (n=121; Placebo, n=58, 48%; Probiotic, n=63, 52%), 167 cases of URI (Placebo=83 cases, 50%, Probiotic, n=84 cases, 50%) were reported during the data collection period. These 167 cases of URI were used to assess the incidence of URI episodes in the total sample, and within and between groups. There were 36 instances (Placebo=13, 36%, Probiotic=23, 64%) where subjects missed the at least two days in a row, and did not communicate via phone, text message or email whether or not they were suffering from a URI on those days; hence, these data were considered missing.

In an effort to examine the incidence of URIs over the course of the study, the self-reported incidence was presented by week and reviewed. The majority of the URI cases occurred during the first five weeks of the data collection period (n=105, 63%; Placebo, n=51, 49%; Probiotic, n=54, 51%), while only 16% (n=27; Placebo, n=14, 17%; Probiotic, n=13, 15%) of URI cases occurred during the last four weeks of the study.

Of the 198 total subjects, 42% (n=84) experienced one URI, while 19% (n=37) of all subjects experienced more than one URI, during the data collection period. The incidence of URIs was not significantly different between the placebo and probiotics groups The questionnaire has three subscales (nasal symptoms, throat symptoms and activity/function items). Therefore, to confirm reliability of the survey, Cronbach's α was calculated separately for each subscale using severity scores on day three of a self-reported URI. Cronbach's α for nasal symptoms, throat symptoms and activity/function items ranged from 0.900-0.964, indicating good reliability. Further, correlations between each item and the total score for each subscale were all greater than 0.6, indicating good correlation.

A limitation in using self-report data to assess URIs is that some URI symptoms are similar to allergy symptoms (for example, rhinorrhea); therefore, it is possible that this study incorrectly classified allergy episodes as URIs. The study attempted to minimize this threat to internal validity by collecting a majority of data during the winter and early spring, excluding subjects with chronic allergies, and randomly assigning subjects to the treatment and comparison group. Additionally, of the 167 URIs reported during the study, only 16% occurred during allergy season; and, the percentage of URIs reported during allergy season was similar between the placebo and probiotics groups (17% and 15%, respectively).

FIG. 8 details the available data from the daily in the total sample (N=198). The effect of probiotics on HRQL during URIs takes into account duration of the illness. Of the 167 URI cases reported during the data collection period (Placebo, n=83 cases, 50%; Probiotic, n=84 cases, 50%), duration was calculated for 158 cases (95%; Placebo=79 cases, 50%; Probiotic=79 cases, 50%) and severity was calculated for 143 cases (86%; Placebo=69 cases, 48%; Probiotic=74 cases, 52%).

Of these 167 cases, there were 119 cases (71%; Placebo=55 cases, 46%; Probiotic=64 cases, 54%) with complete data, wherein, the was completed on all consecutive days of the URI and the day before and day after the URI. Incidence, duration and severity were calculated for all URI cases with complete data.

All URIs with incomplete data (that is, data were missing during a URI or the day before or day after a URI was recorded, n=48 cases, 29%) were included in the calculation of incidence, but duration and severity were only calculated in some of these cases as indicated in the methods section (page 109-110) and summarized below:

Of the 48 cases with incomplete data, there were 15 total cases (31%; Placebo, n=10, 67%; Probiotic, n=5, 33%) where subjects missed the on two or more consecutive days during a URI and/or the first or last day of the URI, and communicated that they were 'sick' or 'not sick' on the missing days. These 15 cases were used to calculate duration, but not severity. Of the 48 cases of URI with incomplete data, there were 24 cases (50%; Placebo, n=14, 58%; Probiotic, n=10, 42%) where subjects missed the on one or more non-consecutive days during a URI. In eight of these 24 cases (33%; Placebo, n=4, 50%; Probiotic, n=4, 50%), subjects communicated that they were 'sick' or 'not sick' on the missing day(s). In the other 16 cases (67%, Placebo, n=10, 63%; Probiotic, n=6, 38%), it was assumed the subject was suffering from a URI on the missed day. The aforementioned 24 cases of URI were used to calculate both duration and severity, since daily severity scores were interpolated by averaging severity scores from the day before and day after the missing survey.

Health-Related Quality of Life During Upper Respiratory Infections

In the total sample (N=198), there were 1003 total days of URI (Placebo, n=562, 56%; Probiotic, n=441, 44%). FIG. 1 and the corresponding table provides descriptive statistics pertaining to the duration of URIs in the total sample and by group. Mean URI duration of the placebo and probiotics group is also displayed in FIG. 1. The mean URI duration for the placebo group was 1.5 days longer compared to the probiotics group. Shapiro-Wilk statistic indicated that duration of URIs was not normally distributed for either the placebo or probiotics group (0.865, p<0.0001, and 0.745, p<0.0001, respectively). Therefore, differences between the probiotic and placebo groups were determined using a non-parametric test. Mann-Whitney U test indicated URI duration was significantly greater in the placebo group (Mdn=6) compared to the probiotics group (Mdn=4), U=2530.00, z=−2.07, p=0.001 (one tailed). The placebo group had a mean rank of 86.97 and probiotics group had a mean rank of 72.03.

FIG. 2 and the corresponding table details the severity scores of URIs, generated by the WURSS-21, in the total sample and by group. Mean severity score of each group is also displayed in FIG. 2. There was a 57% difference (i.e., 57-points) in the mean severity score between the placebo group (157.30) and probiotics group (100.43). Shapiro-Wilk statistic indicated that severity scores were not normally distributed for either the placebo or probiotics group (0.743, p<0.0001, and 0.660, p<0.0001, respectively). Therefore, difference between the groups was determined using a non-parametric test. Mann-Whitney U test indicated that URI severity scores was significantly higher for the placebo group (Mdn=88) compared to the probiotics group (Mdn=58), U=1965.00, z=−2.38, p=0.0003 (one tailed). The placebo group had a mean rank of 80.52 and the probiotics group had a mean rank of 64.05.

The analysis for duration and severity was repeated using data that was obtained during weeks 2-12 only. Consistent with results on page 140-143, these additional analyses indicated that duration of URIs was shorter and severity of URIs was lower in the probiotic compared to the placebo group (p<0.01). findings suggest that HRQL was higher in the probiotics group compared to the placebo group.

Of the 167 URIs that occurred during the data collection period, there were 993 days of surveys (placebo, n=518, 52%; Probiotic, n=475, 48%) that were used to explore the contribution of individual URI symptoms (items 2-11 of the WURSS-21) and functional task impairment (items 12-20 of the WURSS-21) to the total severity score. The most frequently reported symptoms for the placebo and probiotics groups appear to be 'runny nose' (n=709, 71%; Placebo, n=356, 50%; Probiotic, n=353, 50%) and 'tired' (n=704, 71%; Placebo, n=370, 53%; Probiotic, n=334, 47%).

As displayed in FIG. 3, a majority of individual symptoms were reported by a higher percentage of subjects in the placebo group compared to the probiotics group. In general, rankings were skewed to the left (positively skewed), with the most subjects ranking individual symptoms with a score of 1 (very mild). However, as displayed in FIG. 4 a higher percentage of subjects in the probiotics group ranked symptoms as less severe (score of one, two, three or four) compared to the placebo group, while a higher percentage of subjects in the placebo group ranked symptoms as more severe (score of five, six or seven) compared to the probiotics group.

The frequency of responses related to the interference of URIs on functional tasks is presented in FIGS. 5 and 6. The least commonly reported functional tasks that were impaired by URIs were 'work outside the home' (n=217, 22%; Placebo, n=133, 61%; Probiotic, n=84, 39%) and 'work inside the home' (n=189, 19%; Placebo, n=123, 65%; Probiotic, n=66, 35%. A higher percentage of subjects in the placebo group reported interference with functional tasks compared to the probiotics group. In general, rankings were skewed to the left (positively skewed), with most subjects ranking functional tasks with a score of 1 (very mildly). However, as displayed in FIG. 5 a higher percentage of subjects in the placebo group ranked functional tasks as more severe (score of four, five, six or seven) compared to the probiotics group.

Of the 198 subjects in the total sample, 19 missed work days (10%, Placebo, n=11, 58%; Probiotic, n=8, 42%) and 49 missed school days (25%, Placebo, n=34, 69%; Probiotic, n=15, 31%) were reported. There were two subjects in the total sample (1%, Placebo, n=1, 50%; Probiotic, n=1, 50%) who missed the weekly survey less than seven days after experiencing a URI, and did not indicate whether they missed work or school due to the URI. Of the 198 total subjects, 94% (n=186; Placebo, n=92, 50%; Probiotic, n=94, 51%) indicated that they did not miss any work days due to a URI.

Of the 198 subjects in the total sample, the majority (n=171, 86%; Placebo, n=79, 46%; Probiotic, n=92, 54%) indicated that they did not miss any school due to a URI. More subjects in the probiotics group achieved zero missed school days compared to the placebo group (difference of n=13, 9.7%). Mann-Whitney U test indicated that the number of missed school days was significantly higher for the placebo group (Mdn=0) compared to the probiotics group (Mdn=0), U=4421.00, z=−0.45, p=0.002 (one-tailed). The placebo group had an average rank of 104.42 and the probiotics group had an average rank of 94.77.

The analysis for missed work and school days due to URI episodes was repeated using data that was obtained during weeks 2-12 only. These additional analyses indicated that the number of missed work days was the same between groups (p>0.05) while the number of missed school days was significantly lower for probiotics group compared to the placebo group, p<0.05 (one-tailed).

REFERENCES

Barrett, B., Brown, R. L., Mundt, M. P., Thomas, G. R., Barlow, S. K., Highstrom, A. D., & Bahrainian, M. (2009). Validation of a short form Wisconsin Upper Respiratory Symptom Survey (WURSS-21). *Health Quality of Life Outcomes*, 7, 76-96.

Berggren, A., Lazou, A., I, Larsson, N., & Onning, G. (2011). Randomised, double-blind and placebo-controlled study using new probiotic lactobacilli for strengthening the body immune defence against viral infections. European Journal of Nutrition, 50, 203-210.

de Vrese M., Rautenberg, P., Laue, C., Koopmans, M., Herremans, T., & Schrezenmeir, J. (2005). Probiotic bacteria stimulate virus-specific neutralizing antibodies following a booster polio vaccination. European Journal of Nutrition, 44, 406-413.

Rautava, S. E., Salminen, S., & Isolauri, E. (2009). Specific probiotics in reducing the risk of acute infections in infancy—a randomised, double-blind, placebo-controlled study. *Br J Nutr*, 101, 1722-1726.

The invention claimed is:

1. A method for hindering or reducing the duration or severity of an upper respiratory tract infection (URI) or a symptom thereof in a human teenager or adult subject in need thereof, comprising administering *Lactobacillus rhamnosus* strain ATCC 53103 and *Bifidobacterium animalis* subsp. *lactis* strain DSM 15954 to the subject in an amount effective to hinder or reduce the duration or severity of the URI or symptom thereof.

2. The method of claim 1, wherein the symptom is one or more selected from the group consisting of a sore throat, a scratchy throat, a cough, hoarseness, and chest congestion.

3. The method of claim 1, wherein the *Lactobacillus rhamnosus* and *Bifidobacterium animalis* subsp. *lactis* are administered in a single composition.

4. The method of claim 1, wherein the subject does not have a URI or symptoms thereof.

5. The method of claim 1, wherein the subject has a URI or symptoms thereof.

6. The method of claim 1, wherein the method is effective to increase Health-Related Quality of Life (HRQL) as assessed by Wisconsin Upper Respiratory Symptom Survey-21 (WURSS-21) in the subject having a URI.

7. The method of claim 1, wherein the method is effective to reduce the median severity score as assessed by Wisconsin Upper Respiratory Symptom Survey-21 WURSS-21) in the subject having a URI.

8. The method of claim 1, comprising administering from about $10^6$ to $10^{12}$ cfu of *Lactobacillus rhamnosus* strain ATCC 53103 and from about $10^6$ to $10^{12}$ cfu of *Bifidobacterium animalis* subsp. *Lactis* strain DSM 15954.

9. The method of claim 3, wherein the composition comprises from about $10^6$ to $10^{12}$ cfu of *Lactobacillus rhamnosus* strain ATCC 53103 and from about $10^6$ to $10^{12}$ cfu of *Bifidobacterium animalis* subsp. *Lactis* strain DSM 15954.

10. The method of claim 1, wherein the method comprises once daily administration of the *Lactobacillus rhamnosus* strain ATCC 53103 and *Bifidobacterium animalis* subsp. *Lactis* strain DSM 15954.

11. The method of claim 1, wherein the method comprises daily administration of the *Lactobacillus rhamnosus* strain ATCC 53103 and *Bifidobacterium animalis* subsp. *lactis* strain DSM 15954 for a period of at least one week.

* * * * *